US006645171B1

(12) United States Patent
Robinson et al.

(10) Patent No.: US 6,645,171 B1
(45) Date of Patent: Nov. 11, 2003

(54) RECONSTITUTING DEVICE FOR INJECTABLE MEDICATION

(75) Inventors: Grenville Arthur Robinson, Cambridge (GB); Michael Anthony Hobbs, Old (GB); Martyn Omar Rowlands, Essex (GB); John Richard Calvert, Essex (GB)

(73) Assignee: Applied Research Systems ARS Holding N.V., Curacao (NL)

(*) Notice: Subject to any disclaimer, the term of this patent is extended or adjusted under 35 U.S.C. 154(b) by 0 days.

(21) Appl. No.: 09/194,873

(22) PCT Filed: Jun. 3, 1997

(86) PCT No.: PCT/GB97/01492

§ 371 (c)(1), (2), (4) Date: Mar. 16, 1999

(87) PCT Pub. No.: WO97/46203

PCT Pub. Date: Dec. 11, 1997

(51) Int. Cl.[7] .............................................. A61M 37/00
(52) U.S. Cl. ........................................................ 604/82
(58) Field of Search .............................. 604/82, 86–92, 604/200, 201, 411, 412, 413, 414, 415, 416

(56) References Cited

U.S. PATENT DOCUMENTS 3,977,555 A * 8/1976 Larson ...................... 215/247
4,507,113 A * 3/1985 Dunlap ........................ 604/71
5,088,996 A * 2/1992 Kopfer et al. .............. 604/415
5,226,900 A * 7/1993 Bancsi et al. ............... 604/411
5,342,346 A * 8/1994 Honda et al. ............... 604/413
5,454,786 A * 10/1995 Harris ......................... 604/88
5,569,191 A 10/1996 Meyer ......................... 604/82
5,827,262 A * 10/1998 Neftel et al. ................ 604/414
6,090,091 A * 7/2000 Fowles et al. .............. 604/403
6,149,623 A * 11/2000 Reynolds ..................... 604/82

FOREIGN PATENT DOCUMENTS

| | | |
|---|---|---|
| FR | 1510549 | 4/1968 |
| GB | 1114238 | 5/1968 |
| WO | 94/13344 | 6/1994 |
| WO | 95/24176 | 9/1995 |

* cited by examiner

*Primary Examiner*—Manuel Mendez
(74) *Attorney, Agent, or Firm*—Dickstein, Shapiro, Morin & Oshinsky LLP

(57) ABSTRACT

A device for reconstituting liquid for medical use by bringing together a first liquid medium contained in a first vessel in the form of a cartridge (3) and a second medium, such as a drug in solid form, contained in a second vessel in the form of a vial (7), the device (19) comprising means (41) for supporting the first and second vessels, and a movable operating member (50) for applying a force to cause the first liquid medium to be delivered at a controlled rate from the first vessel into the second vessel. The first and second vessels may be provided in a pack (70) having liquid transfer means in the form of a needle (10).

32 Claims, 17 Drawing Sheets

L
18
21
3
70
17
16
22
15
10
10a
24
7
23

FIG. 12.
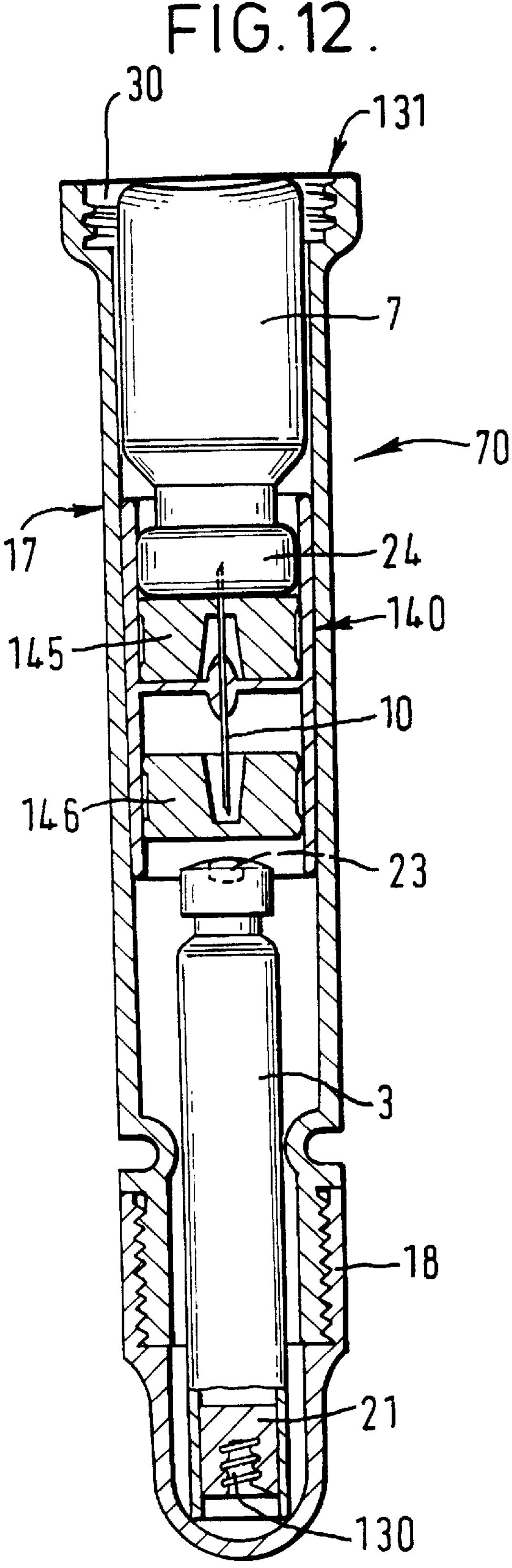
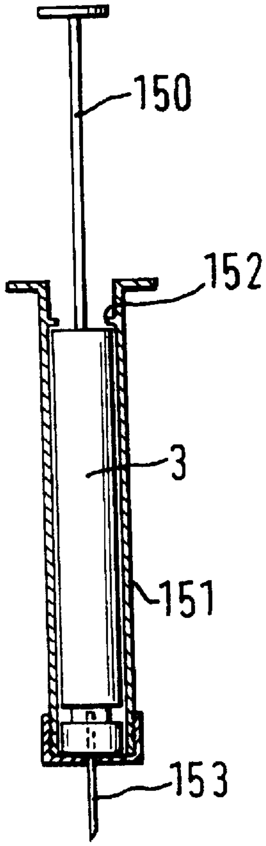
FIG. 15.
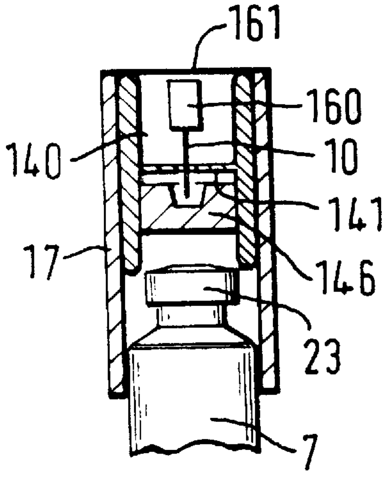
FIG. 16.

RECONSTITUTING DEVICE FOR INJECTABLE MEDICATION

The present invention relates to a device, a pack and a kit for reconstituting a liquid for medical use, such as a parenteral or pharmaceutical liquid.

It is common practice for people requiring frequent parenteral administration of drugs to be provided with home-use kits containing autoinjectors which may be used for the purposes of self-administration. Liquid formulations of drugs are however seldom stable over prolonged periods of time and it is common for the drug itself to be provided in a solid form eg. a lyophilised (i.e. freeze dried), dehydrated or crystalline form. Typically, a user might be provided with a two weeks' supply of a lyophilised drug in sealed vials together with a supply of cartridges containing diluent. However, one problem associated with conventional autoinjector devices is the lengthy procedure (in excess of 40 steps) needed to reconstitute the solid drug into a liquid formulation prior to administration.

A known drug reconstitution device is illustrated in FIG. 1 of the accompanying drawings. In normal use, a plunger pin 1 is screwed into a plunger 2 in a cartridge 3 which contains a diluent for the drug. The cartridge 3 is placed into a barrel 4 of a dismantled autoinjector and a collar 5 is screwed onto a thread 11 thereby holding the cartridge inside the barrel 4, with the plunger pin projecting outwardly of the barrel. A vial 7 containing a drug in solid form has a flip-off plastic seal **7*b* on a bung 7*a*. The seal 7*b* is removed and the exposed portion of the bung is sterilised with an alcohol swab. The drug vial 7 is slid into the end of an adapter 8. A needle 10 is screwed onto a thread 6*a* of the barrel 4 and an outer needle cover 12 and an inner needle cover 13 are removed. The adapter 8 is then screwed onto a thread 6 of the barrel 4, at which time the needle 10 penetrates the bung 7*a* of the drug vial 7**.

To effect reconstitution of the drug formulation, the complete assembly is held vertically with the needle pointing upwards and the plunger pin 1 is gently depressed thereby injecting the contents of the cartridge 3 into the vial 7. The whole assembly is inverted and typically left to stand for 5 minutes to ensure complete dissolution of the drug. After ensuring that the plunger pin 1 is fully depressed the complete assembly is held vertically with the needle pointing upwards and the plunger pin 1 is gently pulled out thus drawing the constituted drug formulation into the cartridge. The vial adapter 8 is then unscrewed from thread 6 and discarded along with the empty vial 7. With the needle pointing vertically upwards, the plunger pin 1 is gently depressed until a few droplets of liquid appear at the end of the needle to ensure that any air trapped within the cartridge is removed. The inner needle cover 13 and the outer needle cover 12 are replaced onto the needle prior to the needle 10 being unscrewed from thread **6*a* and discarded. The plunger pin 1 is unscrewed from the plunger 2 and the collar 5 from thread 11** and both may be discarded. The reconstitution process is now complete and the charged cartridge may be loaded into an autoinjector which may be re-assembled and primed ready for use.

Added to the problem of the lengthy reconstitution procedure, it has also been observed with devices of this type that foaming may occur when the cartridge contents are introduced to the vial. This undesirable effect is limited to a certain degree provided that the user follows the recommended procedure and holds the assembly with the needle pointing upwards before gently depressing the plunger and injecting the liquid vertically upwards into the drug vial.

However the lack of control which the user is generally able to exert over the transmission of the liquid diluent onto the drug means there is still a considerable risk of foaming and associated unwanted effects, especially if the diluent is injected into the vial too rapidly. It is difficult for the user to be able reliably to control the rate at which diluent passes into the vial to avoid foaming on each occasion that the device is used.

Thus viewed from one aspect the present invention provides a device for reconstituting a liquid for medical use by bringing together a first liquid medium contained in a first vessel and a second medium contained in a second vessel, the device comprising means for supporting the first and second vessels, and a movable operating member for applying a force to cause the first liquid medium to be delivered at a controlled rate from the first vessel into the second vessel.

Since the device both supports the first and second vessels and provides a force for causing controlled delivery, this saves a user from performing these tasks and thus simplifies operation. In general, too rapid delivery can be avoided, substantially minimising effects such as foaming with certain media.

The device according to the invention is most convenient for reconstituting solid drugs (e.g. lyophilised drugs in the form of powders or pastes and the like) into a liquid solution or suspension using appropriate solvents, diluents, carriers, etc. However, the device is equally useful for contacting a first liquid (or a first mixture of liquids) with a second liquid or suspension or a mixture of liquids and/or suspensions.

Particular examples of drugs which may be provided in a lyophilised form include growth hormone, fertility drugs, antibiotics (eg. cephalosporins) and renitidine.

Although the first and second vessels may take various forms, in one preferred form of the invention the device is suitable for use with a first vessel in the form of a cartridge with a movable plunger and a second vessel in the form of a vial. The movable operating member of the device can then apply a force to move the plunger and thereby effect delivery.

The media, once brought together, are preferably transferred from the second vessel to the first vessel. It is therefore particularly convenient for the device to be reversibly operable to deliver the media back to the first vessel, e.g. a cartridge, preferably with control of the rate of delivery, although control is not essential during return delivery.

The movable operating member may be driven in various ways, including but not limited to, the use of compressed gas, one or more springs eg. a spring driven motor, or another form of motor eg. an electrically driven motor. In a preferred embodiment, a weight provides the force to effect delivery. In another preferred embodiment, a spring is used.

The rate at which the movable operating member moves will be dependent on a number of factors. In general, the movable operating member will be driven and its movement will be resisted by suitable damping means, for example frictional damping means. In seeking to eliminate unwanted effects such as foaming, it is possible to select e.g. a weight having an appropriate mass or a spring having an appropriate spring constant to provide the drive for the movable operating member and to select components with appropriate frictional interaction in order to give a degree of control over the speed at which liquid is delivered into the second vessel.

Alternative or additional forms of damping may be provided. Thus in a further embodiment of the invention compressed gas may be provided to act against the delivery force whilst being allowed to escape from the region in which it is confined (eg. by bleeding through a small vent). In one preferred embodiment, movement of the movable operating member is controlled at least partly by the flow of gas via a restricted flow path. Alternatively or additionally, there may be hydraulic damping means.

The flow path of the first liquid medium from the first to the second vessel will also tend to introduce its own resistance to flow and will thus have an effect on the rate of delivery. This can be taken into account when designing the device for use with a particular liquid flow path (which may for example be provided by a needle or the like). Account may also be taken of the viscosity of the first liquid medium.

A switch or the like may be provided to initiate delivery. In one preferred embodiment however delivery is initiated by inverting the device. Thus a gravity responsive switch may be provided to actuate e.g. a valve for compressed gas supply or a motor, but where the delivery force is provided by a weight a switch will not normally be needed. In another preferred embodiment in which the drive for the movable operating member is provided by a spring, the spring may be primed and simply released to initiate delivery, or it may be latched in the primed condition.

There is preferably provided a common housing for the means for supporting the first and second vessels and the movable operating member. The device is advantageously a self-contained and portable unit.

The movable operating member is preferably guided in its movement, for example internally of a housing. In certain preferred embodiments, an arrangement of relatively movable coaxial tubular members is provided to guide the movement of the movable operating member. Thus the movable operating member may be movable with a first tubular member which is guided by a second tubular member arranged either outside or inside the first tubular member. In the case where the second tubular member is outside the first, the second tubular member may also conveniently form the housing of the device.

In the case of a weight driven system, the second tubular member may provide the weight to effect delivery and it is then advantageous if it is coaxial with the movable operating member, as this can ensure that load is applied along the axis of movement and not eccentrically.

In general, the movable operating member will be arranged to engage a movable portion of the first vessel to effect delivery, for example by engaging a wall of a bag, bladder, sachet or the like. Preferably the movable portion is urged in an axial direction. The movable portion may for example be a plunger of the first vessel. The movable operating member may be a plunger rod which screws into or otherwise engages such a plunger. Frictional resistance to movement of the movable portion of the first vessel is a further factor which will tend to affect the rate of delivery of the first liquid medium into the second vessel.

An indicator is advantageously provided for indicating the status of delivery. The indicator may provide a visual indication of the position of the movable operating member. Thus, for example, where the movable operating member is located internally of a housing, the housing may be formed with a slot through which the movable operating member is visible to indicate its position. The movable operating member may have a portion projecting through the slot. Alternatively, the indicator may take the form of a timing mechanism independent of the movable operating member but which nevertheless provides an indication that delivery of the first liquid medium into the second vessel is complete. For example, in the case where delivery is initiated by inverting the device, an hourglass may be provided as the timing mechanism.

The device may be provided in combination with a pack removably insertable in the device. Such a combination forms a kit comprising the device and the pack. Such a kit is advantageous for a user because the pack is removable enabling re-use of the device.

Viewed from another aspect therefore the invention provides a kit for reconstituting a liquid for medical use by bringing together a first liquid medium contained in a first vessel and a second medium contained in a second vessel, the kit comprising a pack for holding the first and second vessels, and a device in which the pack is removably insertable, the kit being operable to bring the first liquid medium and the second medium together.

In a preferred embodiment, the device has means for engaging the pack to cause the first and second vessels to be placed in liquid communication, preferably via liquid transfer means of the pack. This further simplifies operation by a user. The device may for example have a lid which as it is closed pushes against the pack and compresses it, thereby causing liquid communication, for example by a needle penetrating through a seal of the first vessel. Preferably, the device has means to ensure that in use the liquid transfer means accesses the second vessel (which may e.g. contain a lyophilised powder) before it accesses the first vessel containing the liquid medium. Where the liquid transfer means is a needle in this preferred embodiment, the fact that the needle penetrates the second vessel before it penetrates the liquid medium containing first vessel prevents the loss of liquid medium.

The pack may include at least the first vessel containing the first liquid medium. The second vessel may be added to the pack by the user or may be added during the manufacture and assembly of the pack, and preferably therefore the pack includes the second vessel containing the second medium.

Preferably the first vessel is readily removable from the pack, so that after the reconstituted liquid has been returned to the first vessel the rest of the pack can be safely disposed of. This reduces the number of steps for the user. In a preferred arrangement, the pack includes liquid transfer means, such as a needle, for liquid transfer between the vessels and this is advantageously shielded by a housing of the pack. Since the liquid transfer means can be disposed of with the pack whilst in a shielded condition, there is improved safety over the known system shown in FIG. 1 in which the needle itself had to be screwed onto and unscrewed from the barrel 4. There is thus increased safety in that the discarded components cannot cause needle-stick injury, because the needle is enclosed within the pack. The housing is preferably sleeve-shaped.

The shielding of the liquid transfer means is of independent patentable significance. Viewed from another aspect therefore the present invention provides a pack for reconstituting a liquid for medical use by bringing together a first liquid medium contained in a first vessel and a second medium contained in a second vessel, the pack comprising means for holding the first and second vessels, liquid transfer means for placing the vessels in liquid communication, said liquid transfer means including a penetrating member for penetrating a closure of the second vessel, and means for shielding a user from the penetrating member before, during and after liquid reconstitution.

A further problem with the known system shown in FIG. 1 is that the needle covers 12 and 13 have to be removed prior to penetration of the bung 7*a* of the drug vial 7 by the needle, so that the needle is exposed to a non-sterile environment. The potential for contamination is even worse if the sharp end of the needle is actually handled by a user.

Viewed from a further aspect, therefore, the present invention provides a pack for reconstituting a liquid for medical use by bringing together a first liquid medium contained in a first vessel and a second medium contained in a second vessel, the pack comprising means for holding the first and second vessels, liquid transfer means for placing the vessels in liquid communication, said liquid transfer means including a penetrating member for penetrating a closure of the second vessel, wherein the penetrating member is arranged to be maintained in a sterile environment at all times prior to penetration of the second vessel closure.

The second vessel closure may form one wall of a sterile chamber, which wall is penetrated when it is desired to communicate the vessels, by relative movement between the wall and the penetrating member. In a preferred arrangement, a protective member for the penetrating member is arranged such that when the penetrating member and the second vessel closure are brought together the penetrating member penetrates both the protective member and the second vessel closure.

The protective member may for example be a sheath on the penetrating member. In use, the penetrating member will pierce the sheath as it penetrates the second vessel closure.

Alternatively the protective member may be a bung which is preferably arranged to be pushed onto the penetrating member by the second vessel. The bung may thus act in the manner of a piston or the like, movable into a sterile chamber surrounding the penetrating member. There is preferably provided means for venting gas from the sterile environment around the penetrating member when the bung is pushed, such as a bead on a wall of a cylinder in which the bung is slidably mounted.

In a convenient form of construction of the pack, the liquid transfer means may be arranged in a tubular housing for receiving the first vessel at one end and the second vessel at the opposite end.

The second vessel is preferably removably held by the pack. This enables more than one second vessel to be used with the first vessel, which is useful for example to produce different concentrations of drug in a diluent.

It will be appreciated that the sterility of the penetrating member can be maintained even if the second vessel is suppled separately of the pack for user assembly therewith. This may be advantageous in that the pack can be manufactured independently of the second vessel.

In one preferred form of the pack, the liquid transfer means includes a second penetrating member for penetrating a closure of the first vessel. Thus the liquid transfer means may for example be a double ended needle. Such an arrangement may be useful if the first vessel is a cartridge closed at one end by a penetratable seal. The arrangement may be such that the sterility of the second penetration member is maintained at all times prior to penetration of the first vessel closure, as with the first mentioned penetrating member. This may be achieved by a protective member such as a sheath or a bung, even if the first vessel is supplied separately of the pack.

In another preferred form of the pack, the liquid transfer means includes a Luer fitting. This may be useful if the first vessel is a pre-filled syringe. The Luer fitting may be kept sterile prior to installation of the first vessel by a paper or film seal or the like.

The pack may be provided with a removable cap which is preferably tamper evident. If the first vessel has a movable portion, such as a plunger, the cap preferably attaches to the pack housing adjacent to the movable portion. Thus removal of the cap enables the movable operating member of the device to engage the movable portion, preferably by a screw-fit.

It will be appreciated that the packs described above have advantages over known constitution systems, such as that described in FIG. 1, which arise independently of the liquid reconstitution device also described: Although the packs may be used with the device, they can also be used on their own, without the device. For example, a user may manually operate a plunger of a cartridge forming the first vessel to bring together the first and second media.

It is envisaged that the device, kit and pack according to the invention in its various aspects will be used by doctors, dentists and the like but particularly by home-users. The invention in a still further aspect thus provides use of a device as hereinbefore defined for reconstituting a pharmaceutical liquid formulation, preferably a parenteral liquid formulation comprising a drug and a diluent or carrier.

Certain preferred embodiments of the invention will now be further described by way of example and with reference to FIGS. 2 to 6 of the accompanying drawings, in which:

FIG. 1 illustrates a known drug reconstruction device;

FIGS. 2*a* and 2*b* show a fully assembled device according to one embodiment of the invention;

FIGS. 3*a* to 3*d* show a pack in various stages of assembly;

FIGS. 4*a* to 4*e* show the assembled pack loaded into a device at various stages of the constitution process;

FIG. 5 shows an alternative form of pack;

FIGS. 6*a* to 6*b* show various stages of the liquid reconstitution procedure;

Figure 7:
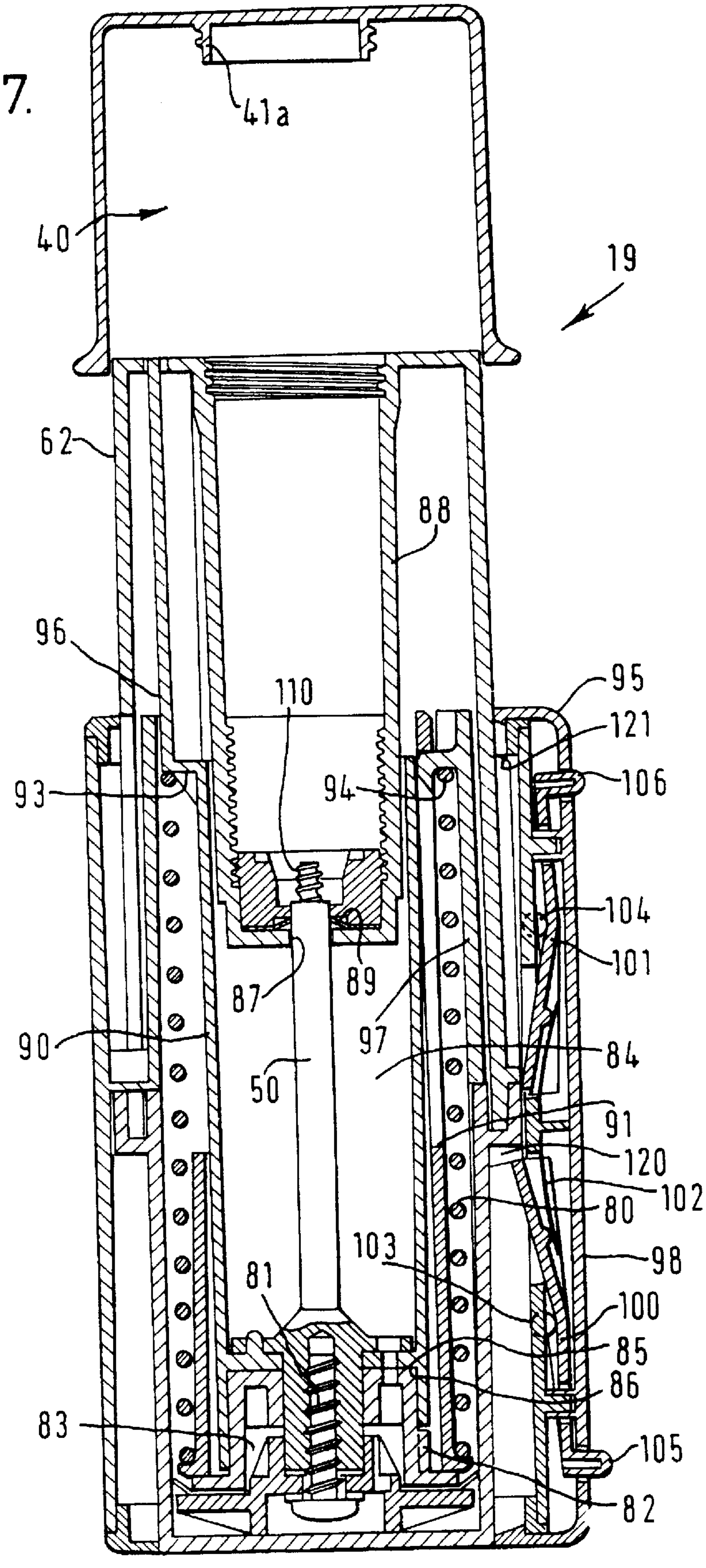
FIG. 7 shows an alternative form of a device for receiving a pack, in a neutral condition.
Figure 13:
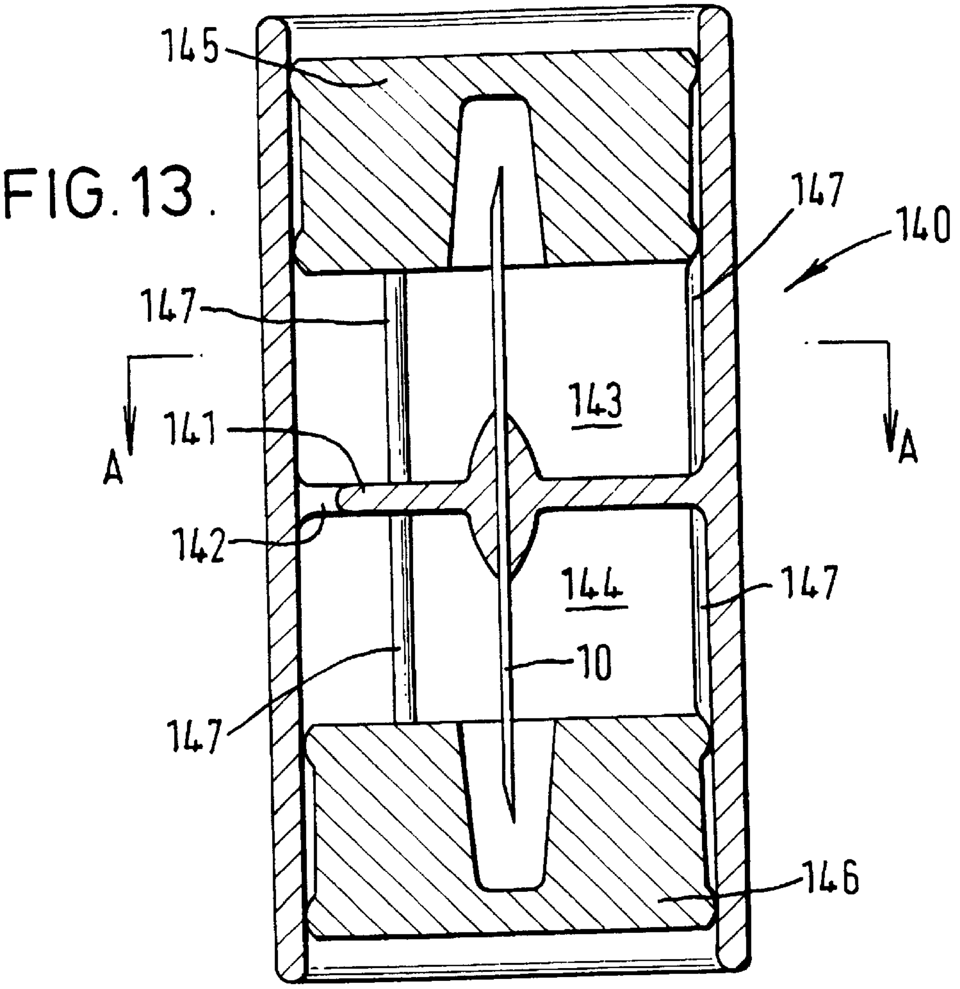
Figure 14:
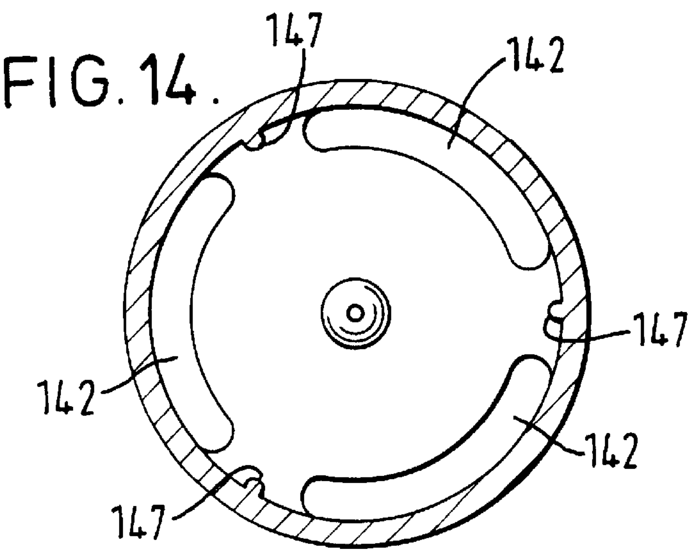

FIGS. 11*a* to 11*i* show various stages of the liquid reconstitution procedure using the device of FIG. 7;

FIG. 12 shows a further alternative form of pack;

FIG. 13 shows a sectional view of part of the pack of FIG. 12;

FIG. 14 shows a sectional view on the lines A—A of FIG. 13;

FIG. 15 shows a syringe formed using the cartridge shown in FIG. 12; and FIG. 16 shows another form of pack.

Figures 3A, 3B, 3C, 3D:
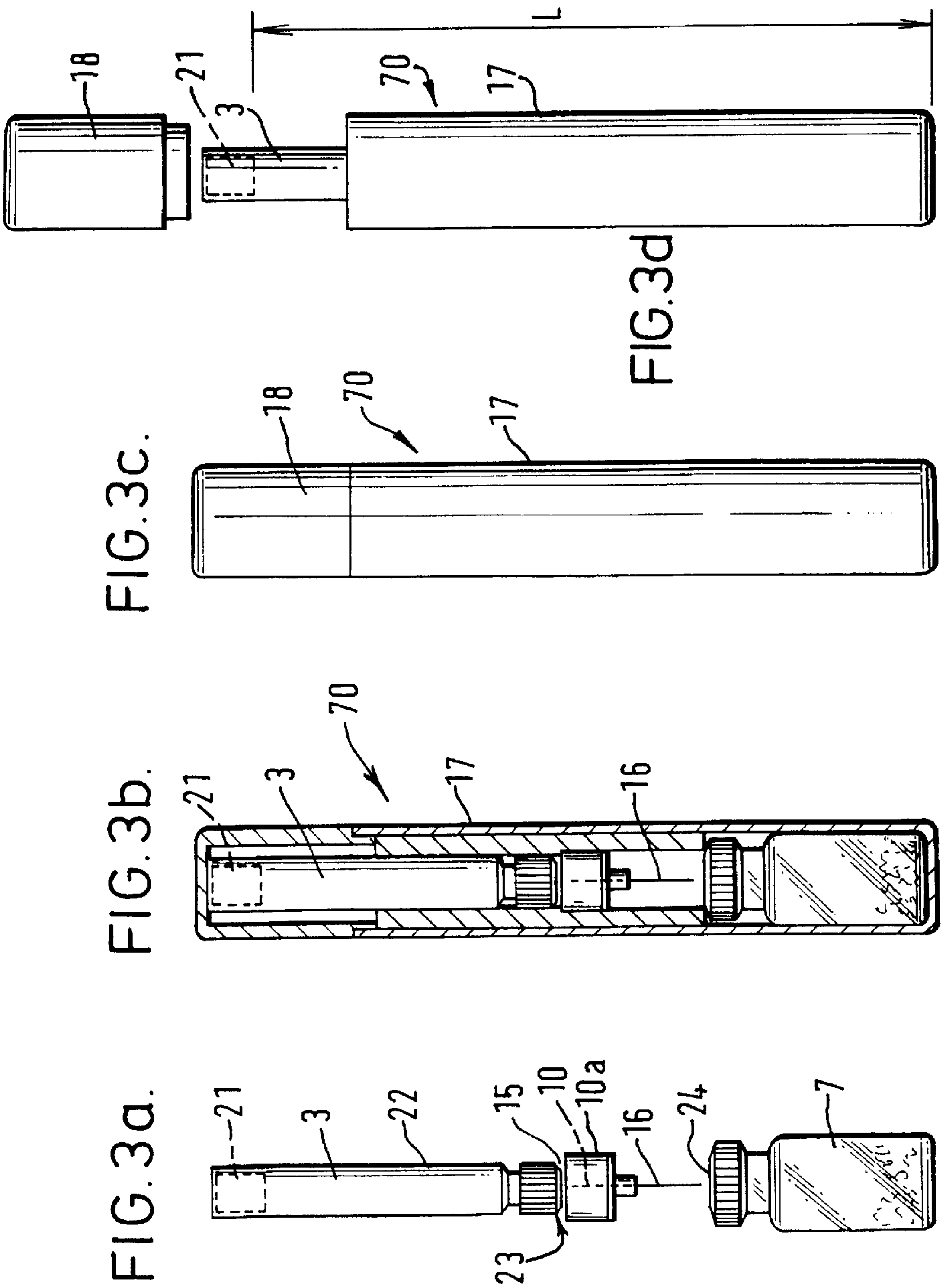

A unitary pack 70 is shown in FIGS. 3*b*–3*d*. This pack comprises a first vessel, in the form of a diluent cartridge 3, and a sterile needle 10 carried by a needle hub 10*a* in a sleeve-shaped housing 17. The cartridge 3 has a plunger 21 at one end and a seal 23 at the other end, adjacent the needle. The end of the needle hub 10*a* nearest to the cartridge may conveniently be covered with any conventional seal 15, such as a paper seal, for example a Tyvek (registered trade mark) seal, to retain its sterility and its other end 16 may be protected by for example a rubber sheath (not shown) to retain sterility. A tamper evident cap 18 closes the end of the housing 17 adjacent the cartridge 3. At the other end of the housing there is disposed a second vessel, in the form of a vial 7 sealed by a bung 24, containing a drug in solid form.

Figure 5:
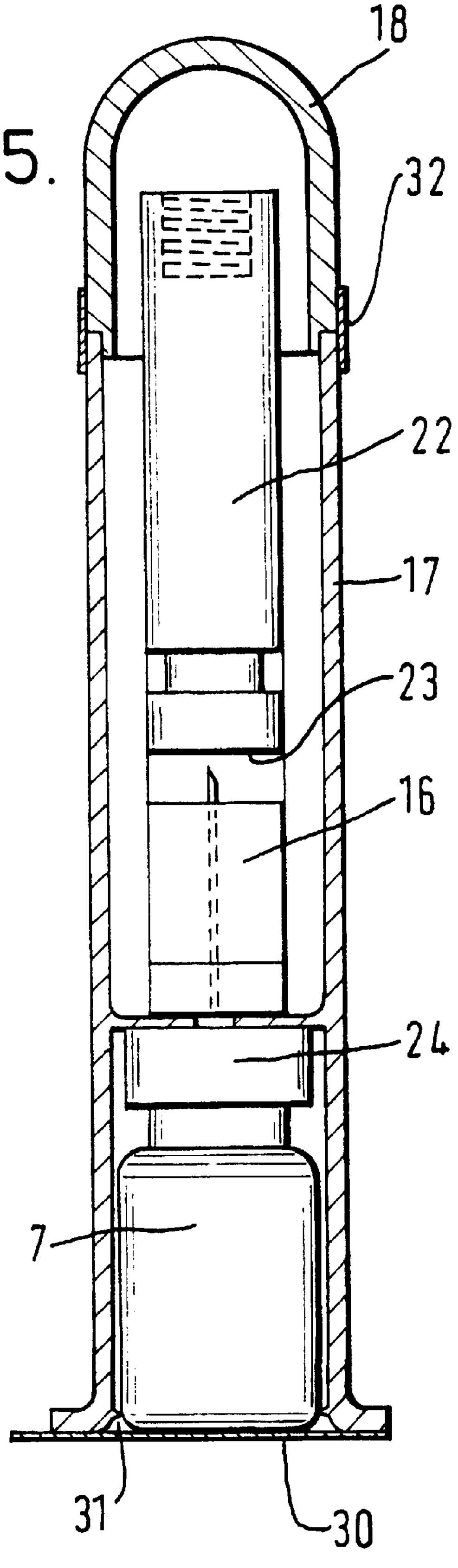

An alternative pack is illustrated in FIG. 5. As shown in FIG. 5, the housing 17 may conveniently be provided with a retention lip 31 which prevents a drug vial 7 being removed from the pack once it has been inserted. A seal 30 closes the end of the housing where the vial 7 is to be inserted. A tamper evident label 32 extends across the join between the housing and the cap 18.

FIGS. 2*a*, 2*b* and 4*a*–4*e* show a device 19 into which the pack 70 is removably insertable. The device 19 has a housing 62 having a screw fitted lid 40 provided with a recess 41 in which the portion of the pack holding the vial 7 engages. Internally of the housing 62 there is provided control means comprising an operating member in the form of a plunger rod 50 and a tubular weight 20 arranged coaxially therewith. The plunger rod 50 has a threaded end for screwing into the plunger 21. An externally projecting member 60 projects from the tubular weight 20 through a slot 61 in the housing 62 of the device 19.

In use, the operator removes a flip-off cover (not shown) from the top of a bung 24 of the drug vial 7 and the seal 30 (see FIG. 5) from the end of pack housing is 17 and, after ensuring the sterility of the bung 24 in the vial, clips the vial into the end of the pack 70. The tamper evident cap 18 is removed from the pack and the pack is inserted into the reconstitution device 19 shown in FIGS. 4*a*–4*e*. It is screwed into position, so that the plunger rod 50 screws into the plunger 21.

In the preferred arrangement illustrated in FIGS. 4*a*–4*e*, the device is arranged to compress the pack, from its initial length to the length “L” shown in FIG. 3*d*. This forces the end 16 of the needle through its rubber sheath and then through the bung 24 on the top of vial 7. The seal 23 of the cartridge is forced through the seal 15 of the needle hub and is then penetrated by the needle 10. The compression is achieved by the lid 40 as it is screwed into place.

Figure 1:
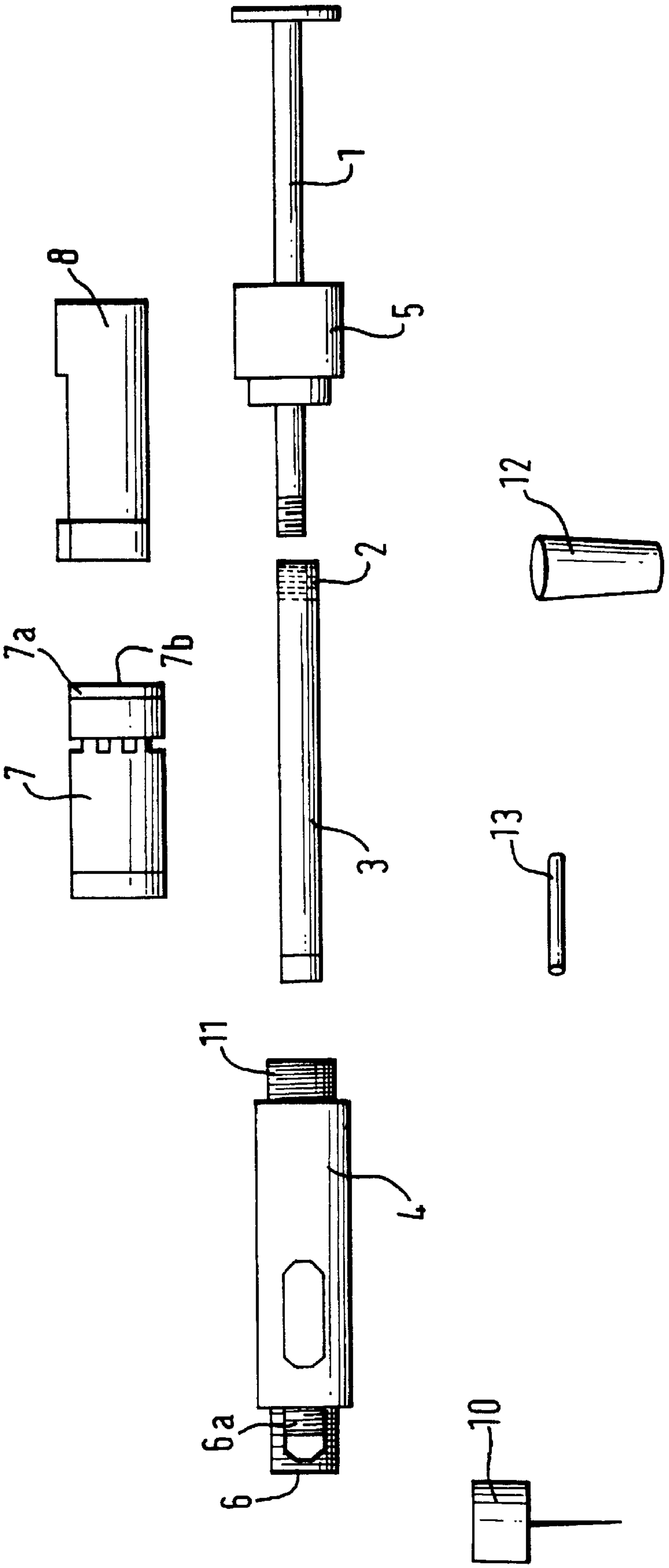
Figure 2A:
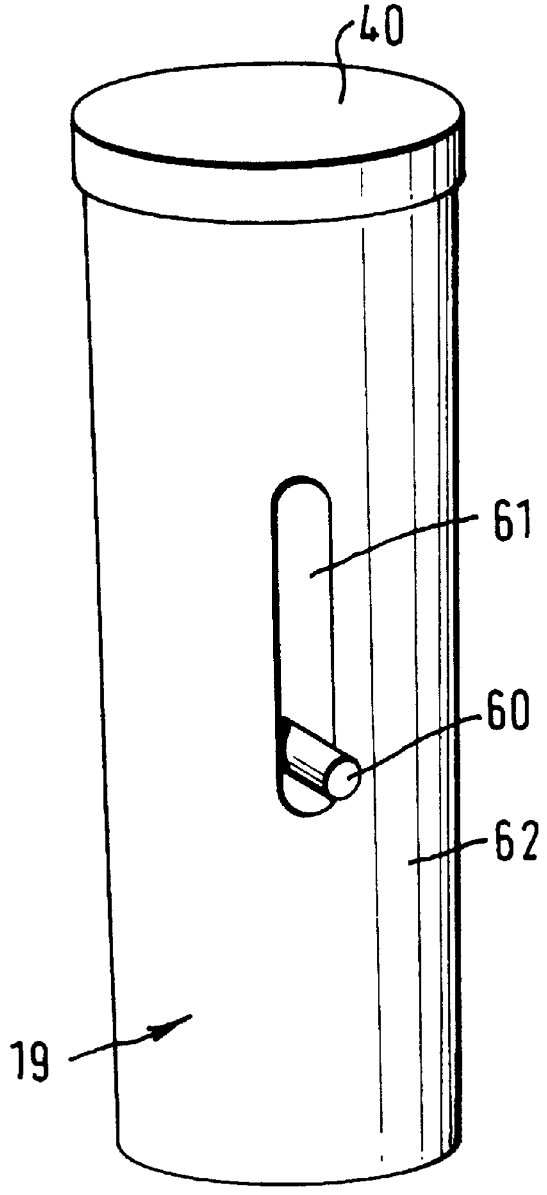
Figure 2B:
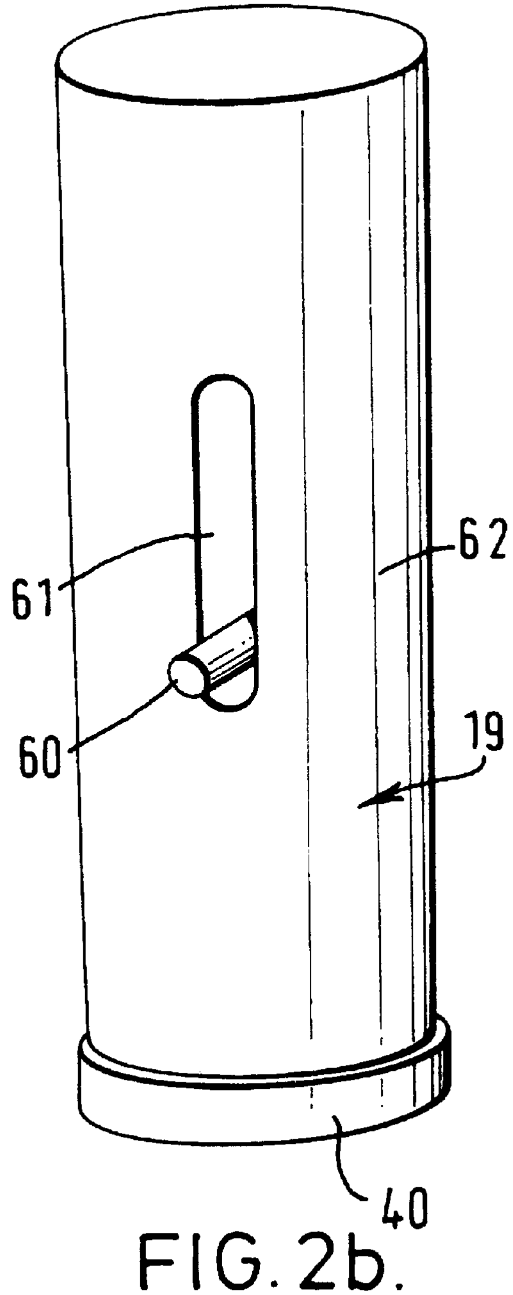
Figure 4A:
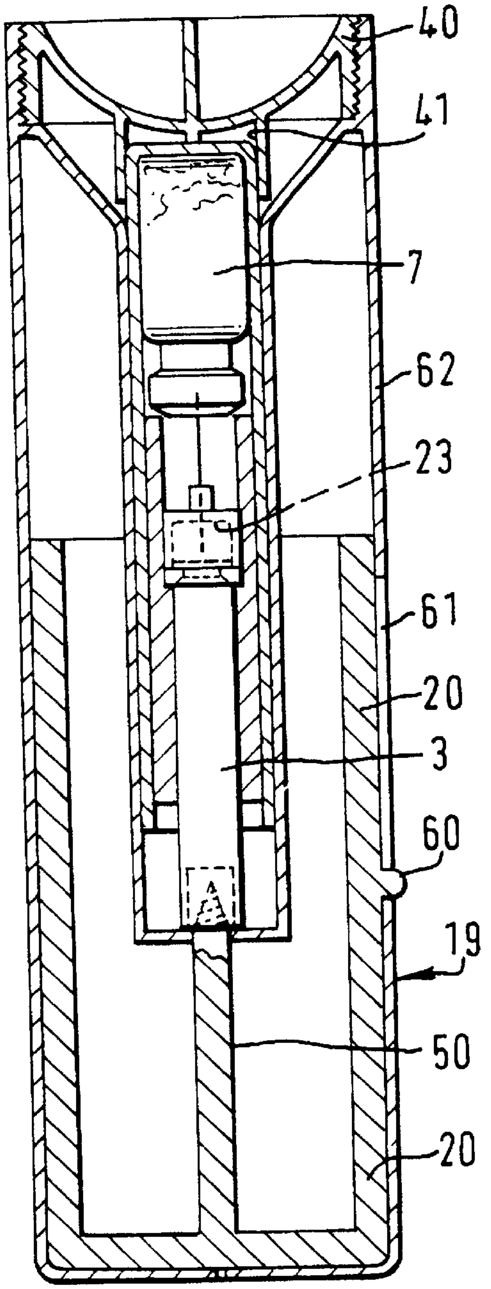

The situation after the needle 10 has penetrated through the bung 24 and the seal 23 is shown in FIG. 4*a* (and FIG. 2*a*). The further steps in the process will be described with reference to FIGS. 4*b*–4*e*.

Figure 4B:
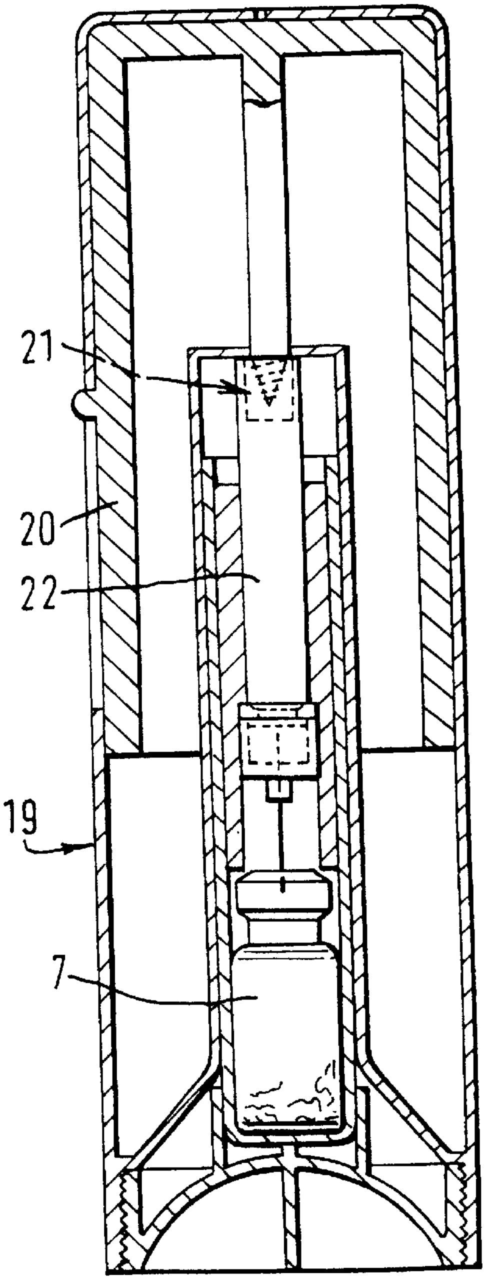

The device 19 is inverted to adopt the position shown in FIG. 4*b* and this causes the tubular weight 20 to move under the effect of gravity, depressing plunger 21 in the cartridge and thereby forcing diluent 22 into the vial 7. The device adopts the position shown in FIG. 4*c* (and 2*b*). The weight 20 is arranged to cause the smooth, gentle movement of plunger 21. The weight therefore provides the drive of the control means. The drive is thus effected in a controlled manner, substantially automatically and independently of the user, who simply has to invert the device to initiate the process.

Figure 4C:
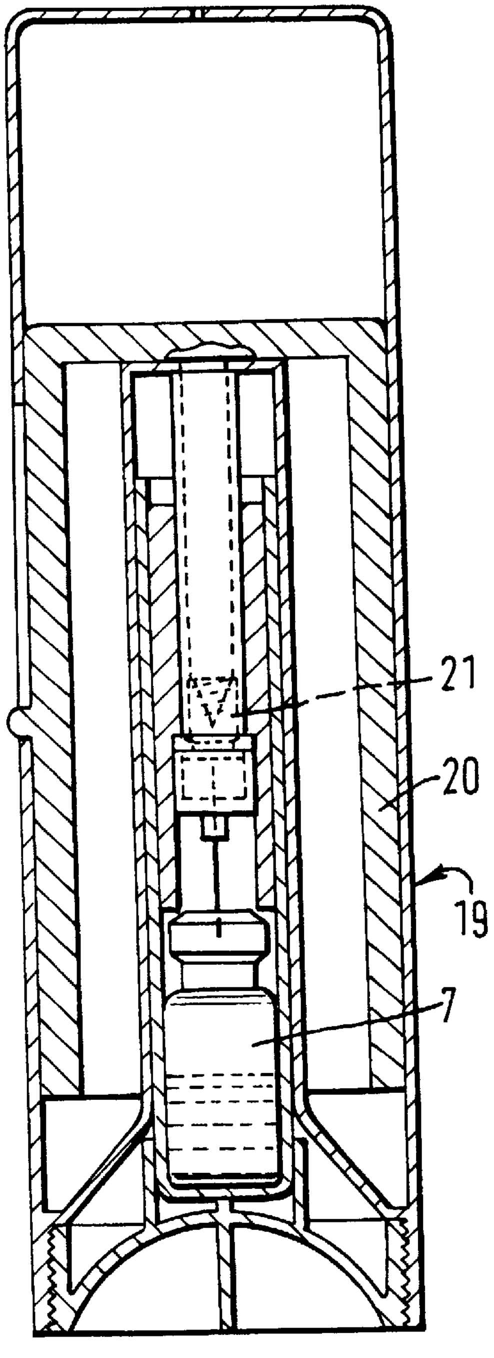
Figure 4D:
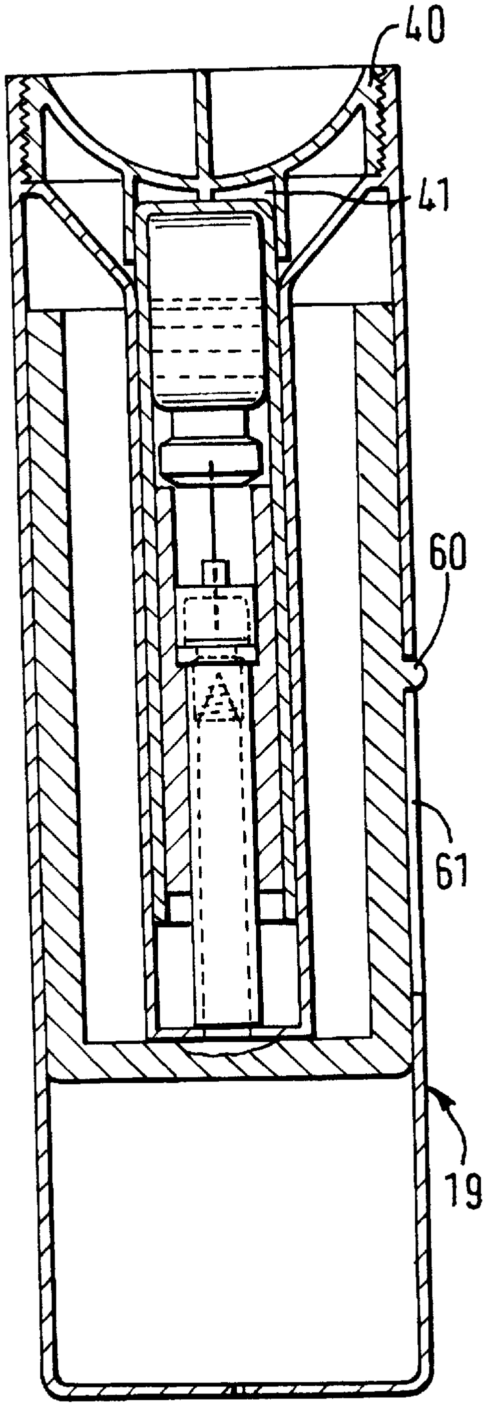
Figure 4E:
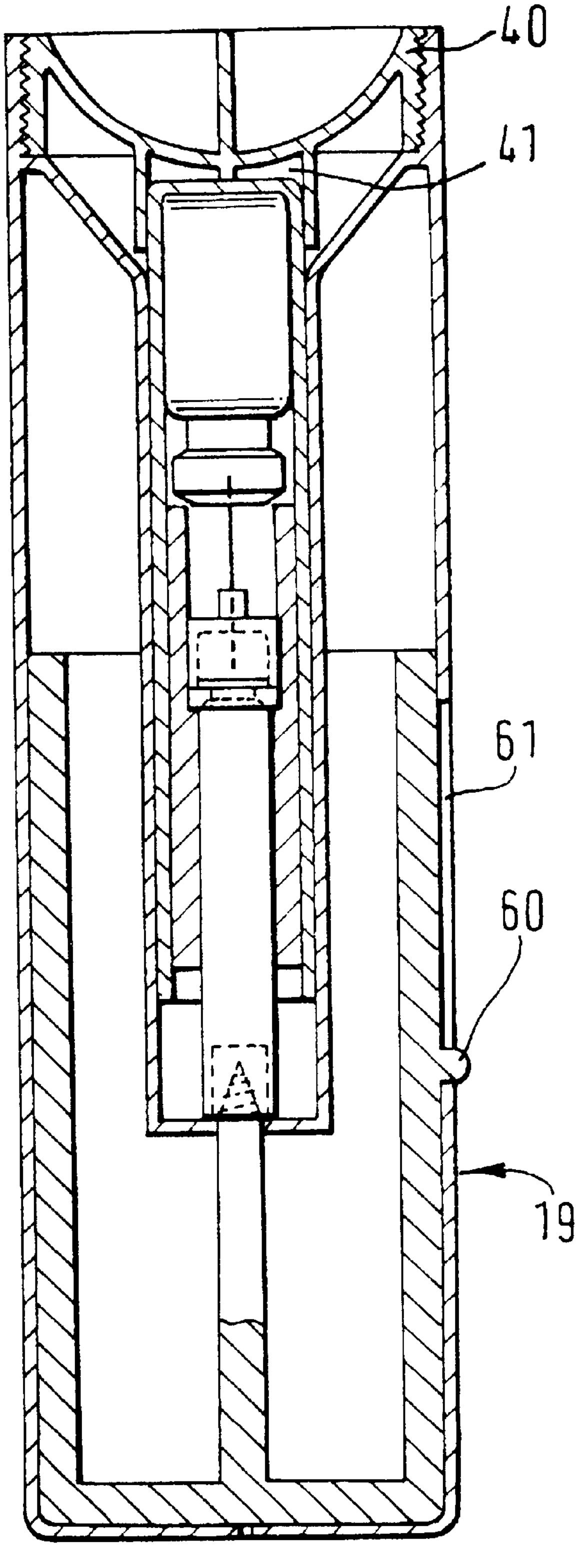

The device is left to stand for several minutes in the position shown in FIG. 4*c* to ensure the complete dissolution of the drug and then inverted once more to the position shown in FIG. 4*d*. This results in weight 20 again moving under the effect of gravity, withdrawing plunger 21 and thereby drawing the constituted drug back into the cartridge 22, as shown in FIG. 4*e*. Disassembly of device 19 allows the pack 70 to be removed therefrom and the cartridge 22 from pack 70, leaving needle 10 and vial 7 in pack 70 for safe disposal. Cartridge 22 is then placed in the autoinjector which is re-assembled and primed for use.

The device is also usefully provided with an externally viewable indicator for indicating the position of the weight so that the user is made aware of when to re-invert the device. This is provided by the member 60 projecting through the slot 61. Alternatively, a timing device such as an hour-glass may be incorporated which is independent of the movement of the control means.

The embodiment described above has the advantage of allowing constitution in a significantly reduced number of steps to that possible with prior art devices. Thus the process of reconstitution in this embodiment is as follows:

1. Open the pack;
2. Remove the flip-off from the drug vial;
3. Insert the drug vial into the pack after ensuring the sterility of the seal on the vial;
4. Insert the pack into the device;
5. Invert the device and leave to stand;
6. Invert the device;
7. Remove the pack; and
8. Remove the cartridge from the pack and use as directed by the physician.

It will be noted that the device is reusable and portable.

Figure 6A:
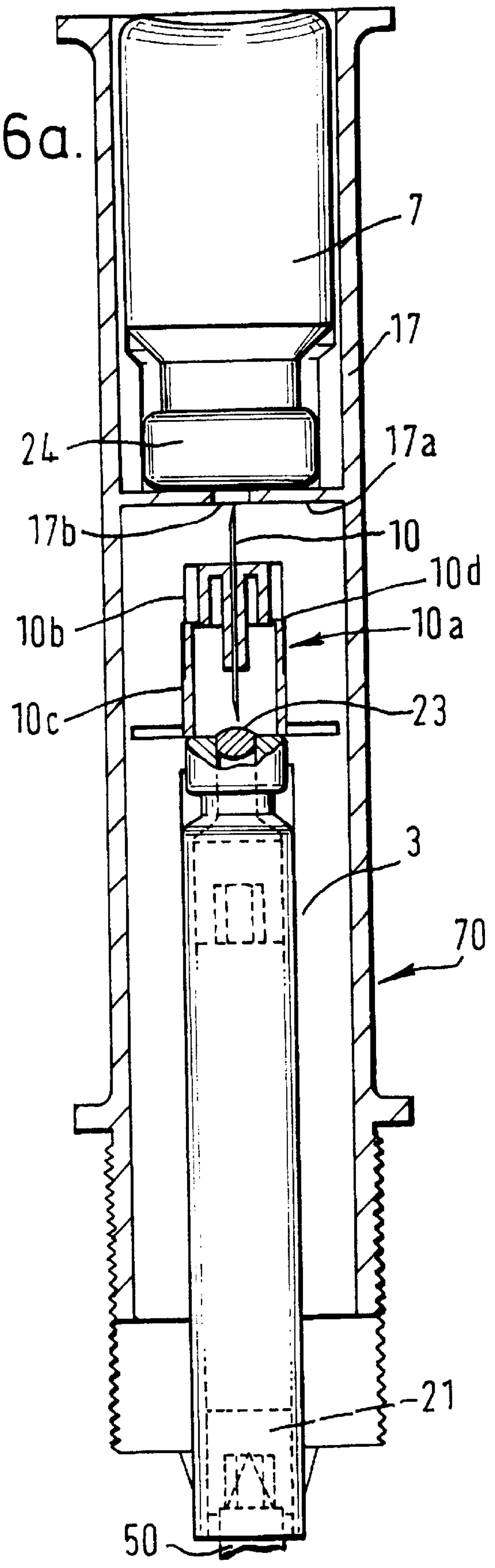
Figure 6B:
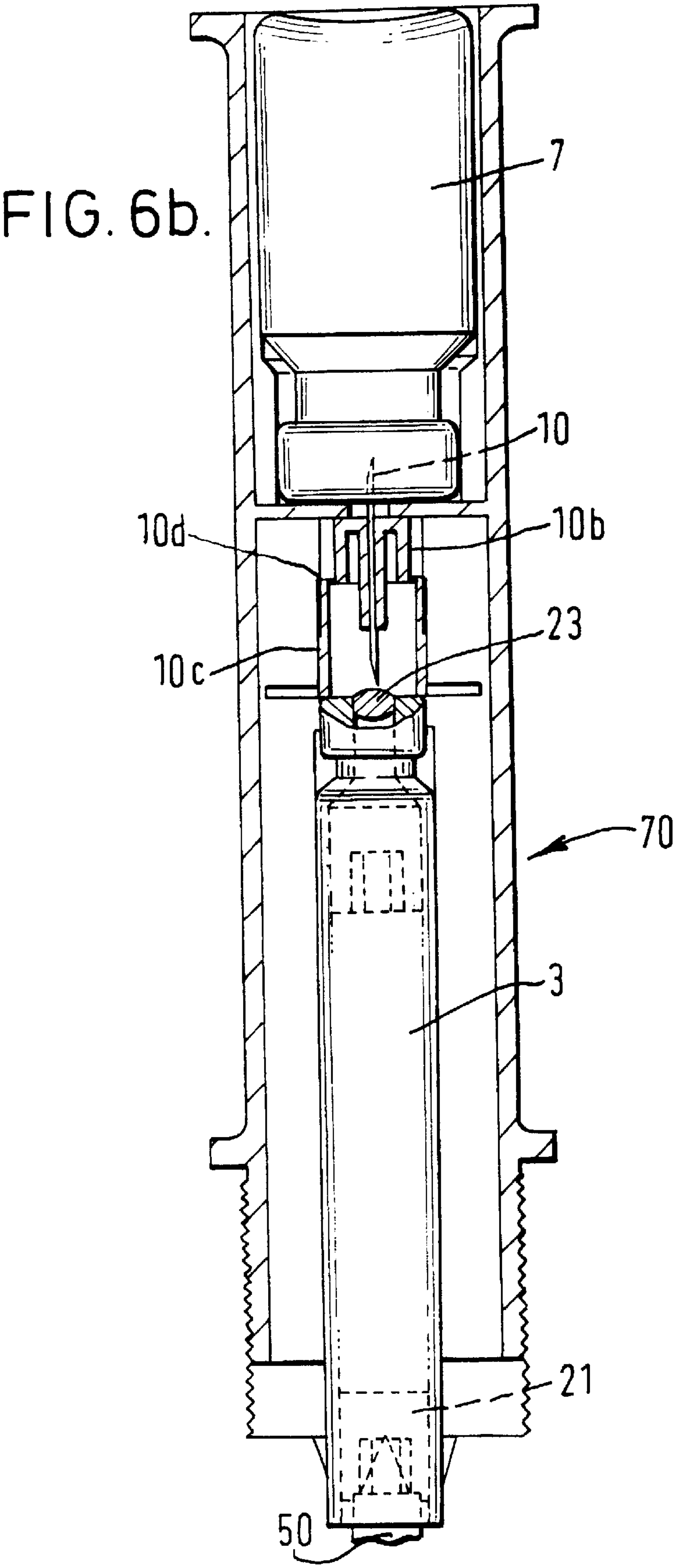
Figure 6C:
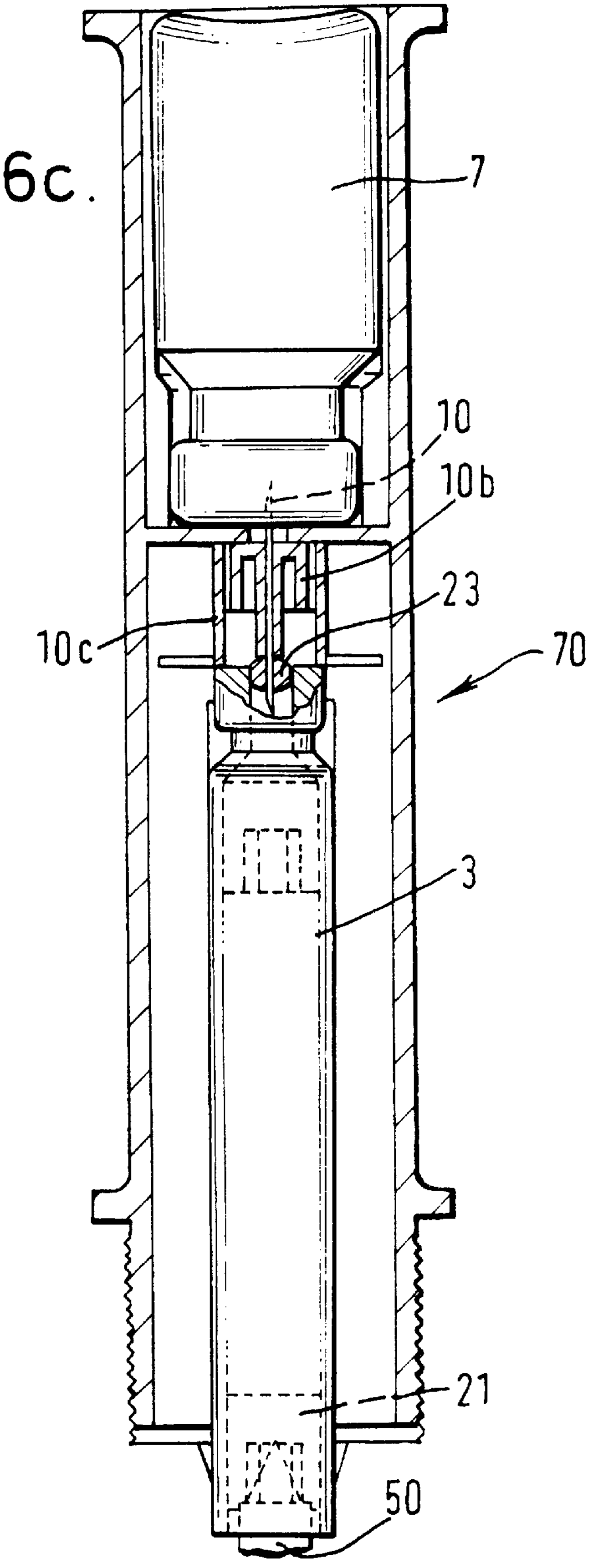

A preferred arrangement for achieving sequential liquid communication between first and second vessels is illustrated in various stages of the procedure in FIGS. 6*a*–6*b*. Thus FIG. 6*a* shows a pack 70 in the initial position prior to compression. A needle 10 is supported by needle hub 10*a* which is itself supported at the inner end of a diluent cartridge 3, the inner end of which is closed by a seal 23. A plunger 21 is provided at the outer end of the cartridge 3 and is threaded to receive a plunger rod 50 which may be an integral part of a device 19 as described hereinbefore. A sleeve shaped housing 17 is provided with a cross-member 17*a* having an opening 17*b* large enough to receive the needle 10. A vial 7 sealed by a bung 24 is disposed on the side of the cross-member 17*a* remote from the cartridge 3. Needle hub 10*a* is in two portions, namely a protruding portion 10*b* which is capable of collapsing within a base portion 10*c* when sufficient force is applied to break a frangible portion 10*d* by which the two portions are adjoined.

FIG. 6*b* shows the arrangement in an intermediate position in which the lid 40 of the device 19 has been partially screwed into place, causing the pack 70 to compress. During the compression movement, the housing 17 and the vial 7 move axially towards the cartridge 3 until the protruding portion 10*b* of the needle hub is engaged against the cross-member 17*a*, as seen in FIG. 6*b*. The needle 10 passes through opening 17*b* to penetrate bung 24 of vial 7.

Further screwing of the lid 40 of the device 19 into a fully closed position completes the compression of the pack 70. The cross-member 17*a* pushes the protruding portion 10*b* towards the cartridge 3, thereby breaking the frangible portion 10*d* and forcing the protruding portion 10*b* to collapse into the base portion 10*c*. The final position in which liquid communication is achieved is shown in FIG. 6*b* wherein the protruding portion 10*b* has collapsed wholly within the base portion 10*c* and the needle 10 has penetrated the seal 23 of the liquid carrying cartridge 3.

Thus the above-described arrangement ensures that the needle 10 penetrates the bung 24 of the vial before it penetrates the seal 23 of the cartridge, thereby avoiding any accidental loss of liquid from the cartridge.

FIG. 7 shows an alternative form of a device 19 for receiving a pack 70, in a neutral condition and before a pack has been added. The principal difference between this device and the one shown in FIGS. 2*a*, 2*b* and 4*a*–4*e* is that the FIG. 7 device is driven by a spring 80, rather than by a weight. This enables the overall device to be lighter and hence particularly convenient to use.

The device 19 has a housing 62 having a lid 40 provided with an external thread 41*a* in which the portion of a pack holding a vial 7 is to engage (e.g. thread 131 shown in FIG. 12). Internally of the housing 62 there is provided a plunger rod assembly including a plunger rod 50 secured by a screw fitting 81 to a plunger hub 82. An air flow path 83 passes through the plunger hub so as to vent a plunger chamber 84 to atmosphere. The air flow path 83 is provided with a pair of paper filters 85,86 which provide a resistance to air flow across the filters and also maintain the cleanliness of plunger chamber 84.

The top end of the plunger rod 50 (as seen in FIG. 7) passes through an opening 87 formed at the lower end of an inner guide tube 88, which is fixed to the external housing 62. The opening 87 is provided with a plunger rod seal 89. The top of the plunger rod is formed with a male thread 110. An outer guide tube 90 extends upwardly from and is fixed to the plunger hub 82 so as to be movable therewith. The outer guide tube 90 is arranged to be guided on inner guide tube 88. A shoulder 93 is provided at the top of outer guide tube 90 and extending upwardly of the shoulder 93 the plunger rod assembly has an indicator flag 96.

A collar 91 is arranged outwardly of outer guide tube 90 so as to be axially movable relative thereto. The spring 80 engages a lower flange of the collar at its lower end and at its upper end it engages both the shoulder 93 of the plunger rod assembly and a shoulder 94 of an actuating assembly 95.

Figure 8:
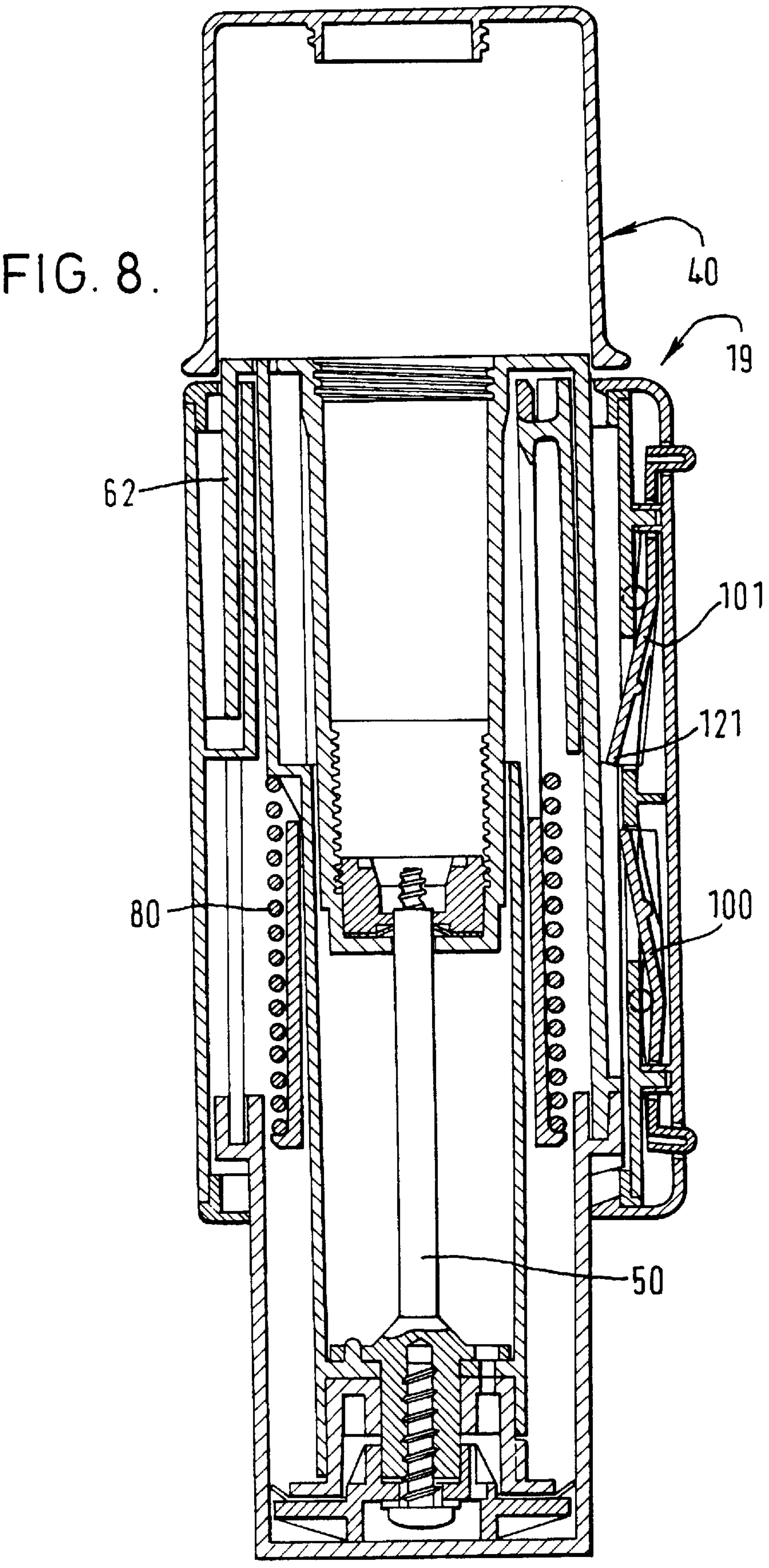
FIG. 8 shows the device of FIG. 7 in a condition primed for delivery.
Figure 9:
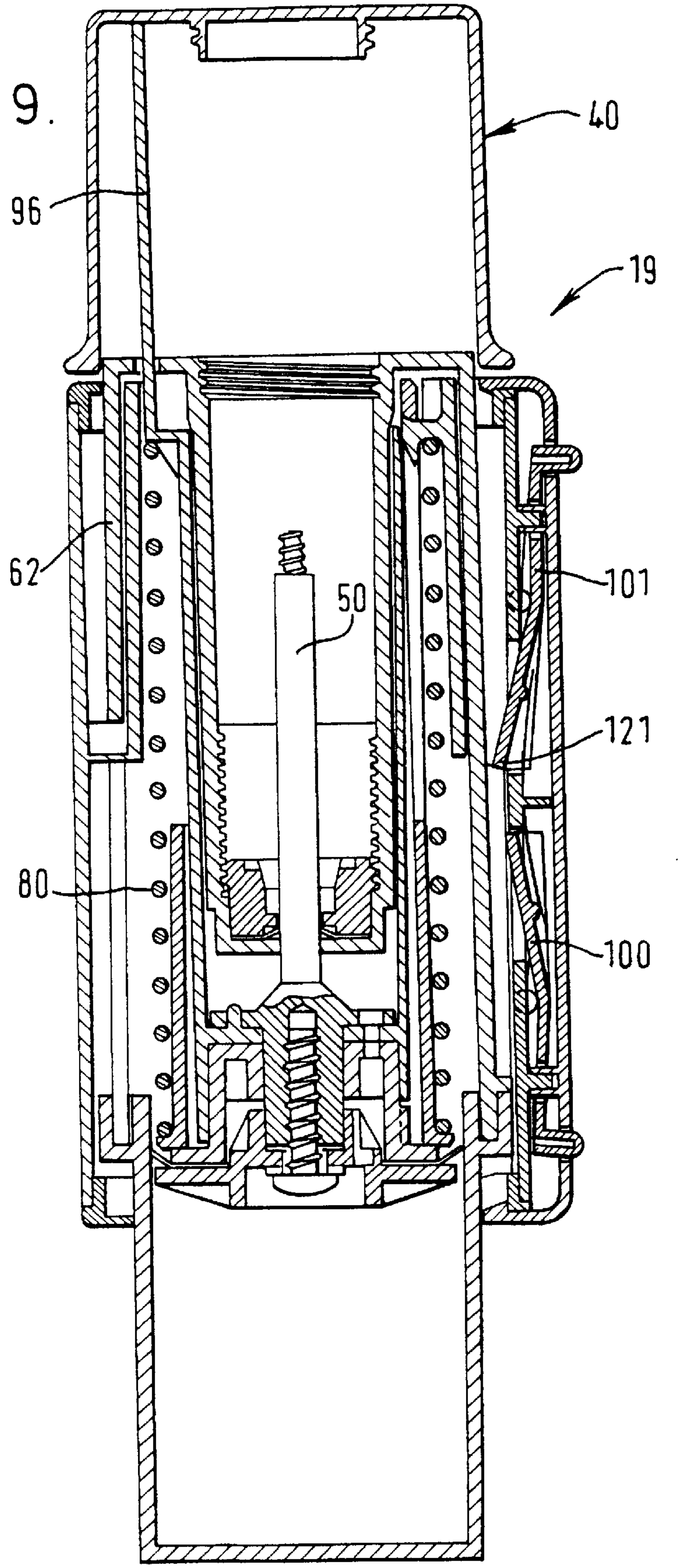
FIG. 9 shows the device of FIG. 7 in a condition after liquid has been delivered from a first vessel to a second vessel.
Figure 10:
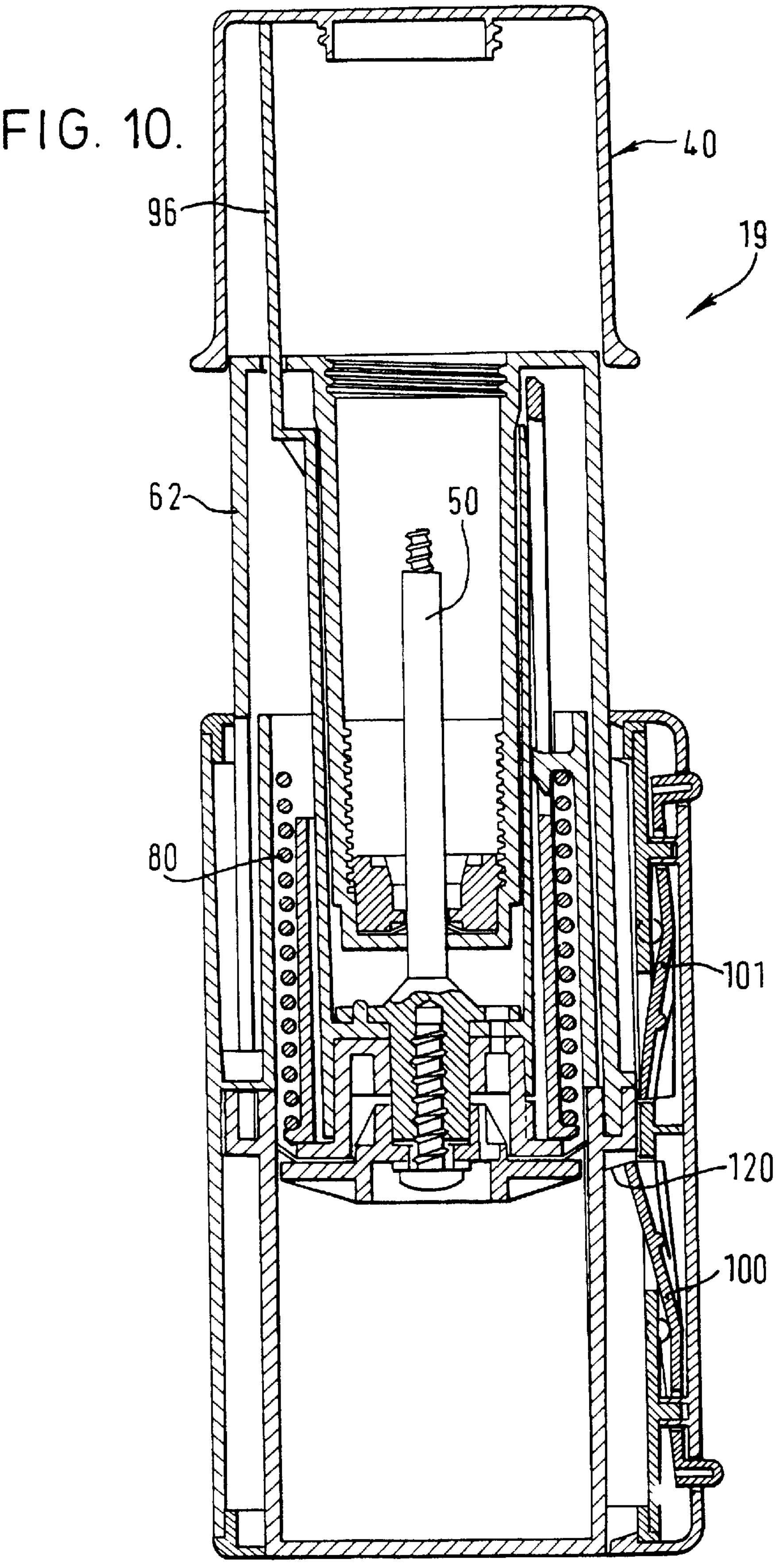
FIG. 10 shows the device of FIG. 7 in a condition primed for delivery of the liquid back to the first vessel.

The collar 91 is slidably supported on the actuating assembly 95 so as to be movable between a lower limit position as seen in FIGS. 7, 8 and 9 and an upper limit position as seen in FIG. 10. The actuating assembly further comprises an inner portion 97 on which the shoulder 94 is formed and which is movable axially inside the housing 62, and an outer sleeve 98 axially movable with the inner portion but situated outwardly of the housing 62.

A lower latch 100 and an upper latch 101 are disposed on the outer sleeve 98 of the actuating assembly. A leaf spring 102 is arranged to urge an upper end of the lower latch 100 and a lower end of the upper latch 101 radially inwardly. The lower latch 100 is arranged to rock about a horizontal axis on a pivot 103, whilst a corresponding pivot 104 is provided for the upper latch 101. Each latch is provided with a respective operating knob 105,106. Detents 120,121 are provided on the housing for engagement by the respective latches 100,101.

Figures 11A, 11B, 11C, 11D, 11E, 11F, 11G, 11H, 11I:
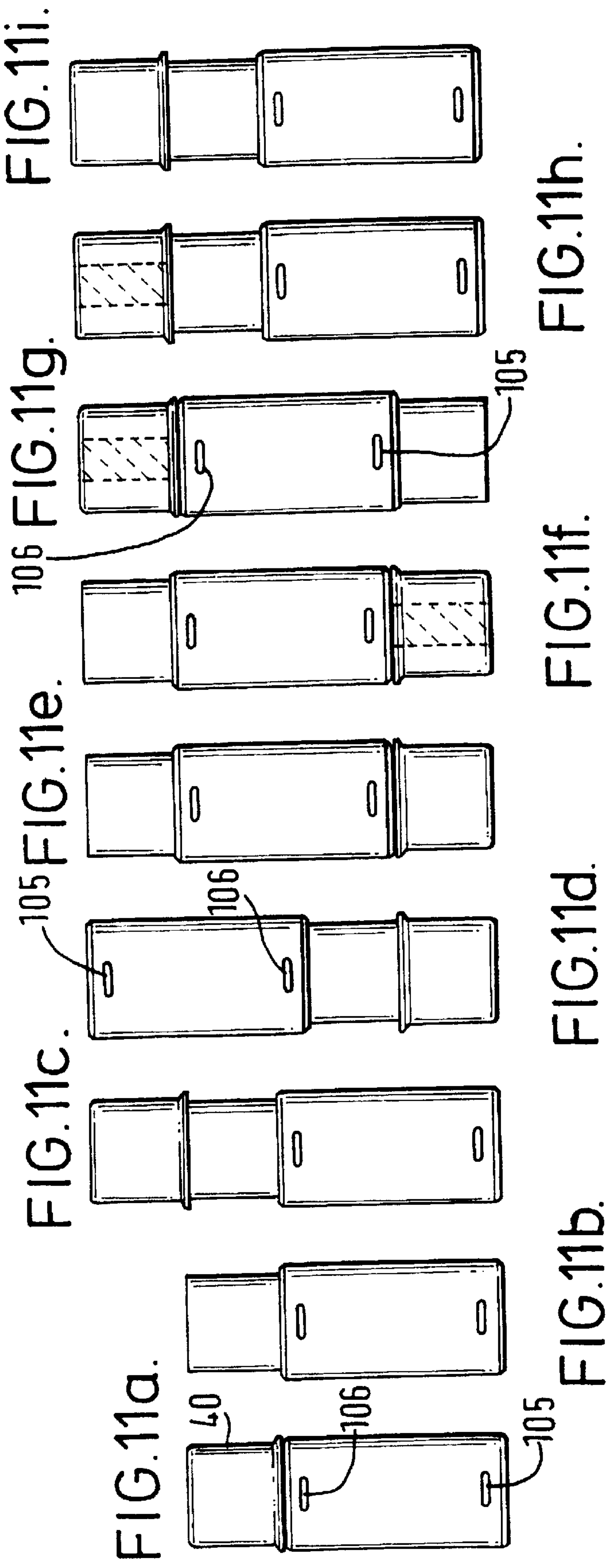

FIGS. 11*a*–11*i* show various stages of the liquid reconstitution procedure using the device of FIG. 7. The procedure will now be described with reference to FIGS. 7–10 and 11*a*–11*i*. The device in its initial condition, without a pack, is shown in FIG. 11*a*. The lid 40 is unscrewed, as shown in FIG. 11*b*, and a pack is screwed into place, with a female thread 130 in a plunger 21 (see FIG. 12) receiving the male thread 110 at the top of the plunger rod 50. The lid 40 is screwed onto the exposed end of the pack, to adopt the position shown in FIG. 11*c*. The device is inverted to adopt the position shown in FIG. 11*d* and operating knob 105 of latch 100 is depressed to cause disengagement of the latch from detent 120. This releases the actuating assembly so that it can be slid downwardly to the position shown in FIG. 11*e*. The device is then in the condition primed for delivery shown in FIG. 8, with latch 101 engaged on detent 121. It will be seen from FIG. 8 that in this primed condition spring 80 is compressed.

Since collar 91 is in its lower limit position it cannot move and thus as spring 80 expands it pushes the plunger rod assembly downwardly (upwardly as viewed in FIG. 8) so as to push liquid from the cartridge 22 into the vial 7. The rate at which the plunger rod assembly moves is determined by the rate of air venting from plunger chamber 84 via the air flow path 83 provided with air filters 85,86. The smaller the pore size of these filters the slower the rate of movement of the plunger rod assembly and a typical target time for the total movement is about 2–3 minutes. As the plunger rod assembly moves downwardly the indicator flag 96 moves downwardly through a slot in the housing 62 so as to be visible through a transparent portion of the lid 40. Use of appropriate graphics on the indicator flag shows when liquid transfer from the cartridge to the vial is complete. This condition is shown in FIGS. 11*f* and 9. It will be seen that latch 101 engages detent 121.

In the next step the device is inverted to adopt the position shown in FIG. 11*g*. The user depresses operating knob 106 to release latch 101 from detent 121 and slides the actuating assembly downwardly until latch 102 engages detent 120, as shown in FIGS. 11*h* and 10. Again this compresses spring 80 which then expands and pushes the plunger rod assembly downwardly, so that the reconstituted liquid is sucked from the vial back into the cartridge. When the indicator flag 96 disappears, liquid transfer back to the cartridge is complete, as shown in FIG. 11*i*. The time taken for return liquid transfer is typically 1–3 minutes. The lid 40 is unscrewed from the device and the pack is unscrewed from the device. The cartridge, now containing the dissolved drug, is removed from the pack and the rest of the pack is discarded. The lid 40 may be screwed back onto the device ready for future use.

A form of pack suitable for use in the device of FIG. 7 is shown in FIG. 12. The pack 70 holds a first vessel, in the form of a diluent cartridge 3, and a second vessel in the form of a drug vial 7. The cartridge 3 has a plunger 21 formed with a female screw thread 130 (for engagement with male screw thread 110 of plunger rod 50 shown in FIG. 7). At the other end the cartridge 3 has a seal 23. The pack 70 has a sleeve shaped housing 17 formed at its end for receiving the drug vial 7 with a thread 131 suitable for engagement with thread 41*a* shown in FIG. 7. Prior to installation of the vial 7, the end of the housing is sealed by a film or paper seal 30. At its other end the pack has a cap 18 which closes the end of the housing 17 adjacent the cartridge 3. When the pack is to be inserted in a device 19 the cap 18 is removed whereby the cartridge 3 protrudes from the housing 17.

A needle assembly 140 is located at a fixed position within housing 17. Referring to FIGS. 13 and 14, the needle assembly 140 comprises a needle hub which is generally "H" shaped in longitudinal cross-section, supporting a double-ended needled 10. A web 141 supports the needle 10 and is formed with apertures 142 which communicate upper and lower sterile needle chambers 143,144. The upper end of upper needle chamber 143 is closed by an axially slidable bung 145, whilst the lower end of lower needle chamber 144 is closed by an axially slidable bung 146. Beads 147 are provided on the inner wall of the needle hub serving both to locate the bungs 145,146 in the positions shown in FIG. 13 and also to vent air from the needle chambers 143,144 when the bungs are pushed onto the needle 10.

FIG. 12 shows the condition of the pack when vial 7 has been pushed into housing 17 such that it pushes bung 145 downwardly to cause penetration by needle 10 of both the bung 145 and the bung 24 which forms the vial closure. It will be appreciated that during the penetration action the sharp end of needle 10 pierces through the two bungs sequentially and is thus maintained in sterile conditions at all times.

Lower bung 146 is shown in FIG. 12 prior to axial upward movement thereof. This will be effected by pushing of the cartridge 3 upwardly (after cap 18 has been removed) to cause the needle 10 to penetrate first through bung 146 and then through seal 23 of the cartridge.

It will be appreciated that whilst the pack 70 shown in FIG. 12 is suitable for use with a constitution device such as that shown in FIG. 7, it may also be used to reconstitute a drug formulation without such a device. Thus a plunger rod 150 (see FIG. 15) may be screwed into thread 130 of plunger 21 and then used manually to push plunger 21 into the cartridge 3. A patient may be supplied with the pack 70 with or without a cartridge 3 and vial 7 already in place. It will generally be preferred for the vial and the cartridge to be preassembled in the pack. The plunger rod 150 may be supplied ready assembled or separately so that the user has to screw it to the plunger 21. The drug vial 7 is first pushed inwardly onto the needle, followed by the cartridge. Plunger rod 150 is used manually to transfer the contents of the cartridge to the vial, the pack is inverted and the reconstituted drug is pulled back into the cartridge. The cartridge is removed from the pack and the pack is thrown away.

A moulded housing 151 for the cartridge is shown in FIG. 15. The cartridge 3 is clipped into the housing 151, where it is held by a lip 152. A standard injection needle 153 is attached to the end of the cartridge 3 and the drug is injected. The syringe and needle are then discarded. Alternatively, the cartridge could be inserted into an autoinjector.

FIG. 16 shows an alternative form of needle assembly 140, for use with a prefilled syringe. This is similar to the design of FIG. 12, except that instead of providing a double-ended needle 10 a Luer fitting 160 is provided. The sharp end of the needle 10 is kept sterile by a bung 146, as in the case of FIG. 12, whilst the Luer end is kept sterile with a seal 161 of a suitable film, such as Tyvek (registered trade mark). To reconstitute the drug a user pushes the vial 7 into the housing 17 so as to push the bung 146 axially. The bung 146 and the seal 23 of the vial 7 are pierced by the needle 10. The seal 161 is then either peeled off and the pre-filled syringe fastened to the Luer fitting or the seal is pierced with the syringe's nozzle prior to attaching the syringe to the Luer fitting. Reconstitution of the drug takes place as described previously and the syringe containing the reconstituted drug is removed. An injection needle is fastened to the syringe and the dose administered. The pack is discarded.

It will be appreciated that the needle hub 140 could be elongated, thus obviating the need for the housing 17. This could make the overall unit less expensive. It will also be appreciated that, as with the FIG. 12 arrangement, the end of the needle 10 which enters the vial 7 is kept sterile at all times and that the vial is preferably removable whereby more than one vial can be used with one syringe of diluent.

What is claimed is:

1. A device for reconstituting liquid for medical use by bringing together a first liquid medium contained in a first vessel, the device comprising a support for the first and second vessels, a moveable operating member, and a driver for automatically moving the moveable operating member for applying a force to cause the first liquid medium to be delivered at a controlled rate from the first vessel into the second vessel, wherein the moveable operating member is reversibly operable to cause the combined first and second media to be delivered from the second vessel into the first vessel.

2. A device as claimed in claim 1, comprising a weight to provide the force to effect delivery.

3. A device as claimed in claim 1, comprising one or more springs to provide the force to effect delivery.

4. A device as claimed in claim 1, wherein movement of the movable operating member is controlled at least partly by the flow of gas via a restricted flow path.

5. A device as claimed in claim 1, comprising a housing which houses the support for the first and second vessels and the movable operating member.

6. A device as claimed in claim 1, wherein an arrangement of relatively movable coaxial tubular members is provided to guide the movement of the movable operating member.

7. A device as claimed in claim 1, wherein the movable operating member is arranged to engage a movable portion of the first vessel to urge the movable portion in an axial direction.

8. A device as claimed in claim 1, comprising an indicator for indicating the status of delivery.

9. A device as claimed in claim 8, wherein the indicator provides a visual indication of the position of the movable operating member.

10. A device as claimed in claim 1, combination with a pack removably insertable in the device.

11. A device and a pack as claimed in claim 10, wherein the pack includes the first vessel containing the first liquid medium, the second vessel containing the second medium, or both.

12. A device and a pack as claimed in claim 10, wherein the pack includes a liquid transfer device for transferring liquid from the first vessel into the second vessel, the liquid transfer device being shielded by a housing of the pack.

13. A device and a pack as claimed in claim 11, wherein the pack has a removable tamper evident cap.

14. A device and a pack as claimed in claim 10, wherein the device has an engagement member for engaging the pack to cause the first and second vessels to be placed in liquid communication.

15. Use of a device as claimed in claim 1, for reconstituting a pharmaceutical liquid.

16. Use as claimed in claim 15, for reconstituting a pharmaceutical liquid formulation comprising a drug and a diluent or carrier.

17. A kit for reconstituting a liquid for medical use by bringing together a first liquid medium contained in a first vessel and a second medium contained in a second vessel, the kit comprising a pack for holding the first and second vessels, and a device in which the pack is removably insertable, the kit being operable to bring the first liquid medium and the second medium together by transferring the first liquid medium from the first vessel to the second vessel and being operable to transfer the combined first and second media from the second vessel to the first vessel, wherein the pack is arranged to hold the first vessel removably so that, in use, after transfer of the first liquid medium from the first vessel to the second vessel and transfer of the combined first and second media from the second vessel to the first vessel, the first vessel may be removed from the pack together with the combined first and second media contained therein.

18. A kit as claimed in claim 17, wherein the device has an engagement device for engaging the pack to cause the first and second vessels to be placed in liquid communication.

19. A kit as claimed in claim 17, comprising a liquid communication device arranged to access the second vessel before it accesses the first vessel.

20. A pack for reconstituting a liquid for medical use by bringing together a first liquid medium contained in a first vessel and a second medium contained in a second vessel, the pack comprising a holder for the first and second vessels, a liquid transfer device for placing the vessels in liquid communication, said liquid transfer device including a first penetrating member for penetrating a closure of the second vessel, a second penetrating member for penetrating a closure of the first vessel, and a shield for shielding a user from the penetrating members before, during and after liquid reconstitution, wherein the pack further comprises protective members for the first and second penetrating members arranged such that when the first penetrating member and second vessel closure are brought together the first penetrating member penetrates both a protective member and the second vessel closure, and when the second penetrating member and the first vessel closure are brought together the second penetrating member penetrates both a protective member and the first vessel closure.

21. A pack for reconstituting a liquid for medical use by bringing together a first liquid medium contained in a first vessel and a second medium contained in a second vessel, the pack comprising a holder for the first and second vessels, a liquid transfer device for placing the vessels in liquid communication, said liquid transfer device including a first penetrating member for penetrating a closure of the second vessel, a second penetrating member for penetrating a closure of the first vessel, wherein the first and second penetrating members are arranged to be maintained in a sterile environment at all times prior to penetration of the first and second vessel closures, and wherein the pack further comprises protective members for the first and second penetrating members arranged such that when the first penetrating member and second vessel closure are brought together the first penetrating member penetrates both a protective member and the second vessel closure, and when the second penetrating member and the first vessel closure are brought together the second penetrating member penetrates both a protective member and the first vessel closure.

22. A pack as claimed in claim 20, wherein the protective members are sheaths on the first and second penetrating members.

23. A pack as claimed in claim 20, wherein the protective members are bungs.

24. A pack as claimed in claim 23, wherein the bungs are arranged to be pushed on e first and second penetrating members by the first and second vessels.

25. A pack as claimed in claim 24, comprising a vent for venting gas from the sterile environment around the first and second penetrating members when the bungs are pushed.

26. A pack as claimed in claim 20, wherein the liquid transfer device is arranged in a tubular housing for receiving the first vessel at one end and the second vessel at the opposite end.

27. A pack as claimed in claim 1, arranged to hold the second vessel removably.

28. A pack as claimed in claim 21, wherein the protective members are sheaths on the first and second penetrating members.

29. A pack as claimed in claim 21, wherein the protective members are bungs.

30. A pack as claimed in claim 29, wherein the bungs are arranged to be pushed onto the first and second penetrating members by the first and second vessels.

31. A pack as claimed in claim 30, comprising a vent for venting gas from the sterile environment around the first and second penetrating members when the bungs are pushed.

32. A pack as claimed in claim 21, wherein the liquid transfer device is arranged in a tubular housing for receiving the first vessel at one end and the second vessel at the opposite end.

* * * * *

UNITED STATES PATENT AND TRADEMARK OFFICE

CERTIFICATE OF CORRECTION

PATENT NO. : 6,645,171 B1 Page 1 of 1
DATED : November 11, 2003
INVENTOR(S) : Michael A. Hobbs et al.

It is certified that error appears in the above-identified patent and that said Letters Patent is hereby corrected as shown below:

Title page,
Item [30], Foreign Application Priority Data should read:
-- Jun. 3, 1996 (GP) …………….. 9611562.1 --.

Signed and Sealed this

Eleventh Day of January, 2005

JON W. DUDAS
*Director of the United States Patent and Trademark Office*